US006902741B1

(12) United States Patent
Grawe et al.

(10) Patent No.: US 6,902,741 B1
(45) Date of Patent: Jun. 7, 2005

(54) LAMINATES CONTAINING AN ACTIVE SUBSTANCE TRANSDERMAL SYSTEM

(75) Inventors: Detlef Grawe, Kleinromstedt (DE); Peter Hoesel, Jena (DE); Wilfried Fischer, Vagen (DE)

(73) Assignee: Jenapharm GmbH & Co. KG, Jena (DE)

( * ) Notice: Subject to any disclaimer, the term of this patent is extended or adjusted under 35 U.S.C. 154(b) by 0 days.

(21) Appl. No.: 09/913,112

(22) PCT Filed: Feb. 8, 2000

(86) PCT No.: PCT/EP00/00983

§ 371 (c)(1),
(2), (4) Date: Mar. 5, 2002

(87) PCT Pub. No.: WO00/47191

PCT Pub. Date: Aug. 17, 2000

(30) Foreign Application Priority Data

Feb. 10, 1999 (DE) .......................... 199 06 152

(51) Int. Cl.⁷ .......................... A61F 13/02; A61L 15/16; A61K 9/14
(52) U.S. Cl. .................. 424/448; 424/449; 424/484; 424/485; 424/486; 424/487; 424/489
(58) Field of Search ................ 424/448, 449, 424/487, 484

(56) References Cited

U.S. PATENT DOCUMENTS

| | | | | |
|---|---|---|---|---|
| 4,409,206 A | * | 10/1983 | Stricker ..................... | 424/444 |
| 4,746,509 A | * | 5/1988 | Haggiage et al. ............ | 424/449 |
| 5,028,435 A | * | 7/1991 | Katz et al. .................. | 424/484 |
| 5,230,898 A | * | 7/1993 | Horstmann et al. ......... | 424/449 |
| 5,232,703 A | * | 8/1993 | Blank ......................... | 424/449 |
| 5,656,286 A | | 8/1997 | Miranda et al. | |
| 5,702,721 A | | 12/1997 | Horstmann et al. | |
| 6,312,715 B1 | * | 11/2001 | Cantor et al. ............... | 424/448 |

FOREIGN PATENT DOCUMENTS

| | | |
|---|---|---|
| DE | 43 32 284 A1 | 3/1995 |
| DE | 43 32 283 A1 | 4/1995 |
| DE | 43 34 553 A1 | 4/1995 |
| DE | 44 05 898 A1 | 8/1995 |
| DE | 44 29 397 A1 | 2/1996 |
| DE | 44 29 398 A1 | 2/1996 |
| DE | 197 01 949 A1 | 7/1998 |
| DE | 198 09 845 A1 | 9/1999 |
| EP | 0 481 443 A1 | 4/1992 |
| EP | 0 516 141 A1 | 12/1992 |
| FR | 0 674 900 A1 | 10/1995 |
| WO | 98/26762 | 6/1998 |

OTHER PUBLICATIONS

Shuji Kondo et al: "Enhancement of Transdermal Delivery . . . " In J. Pharmacobio–Dyn. 10, 1987, pp. 743–749 (In English).
Shuji Kondo et al: "Enhancement of Transdermal Delivery . . . " In J. Pharmacobio–Dyn. 10, 1987, pp. 662–668 (In English).
H.P. Merkle: "Bildung Und Charakterisierung Uebersaettinger . . . " In Pharm. Ind. 42, NR. 10, 1980, pp. 1009–1018. (English Abstract Is Provided).
M.F. Coldman et al: "Enhancement of Percutaneous Absorption . . . " In Journal of Pharmaceutical Sciences, vol. 58, No. 9. Sep. 1969, pp. 1098–1102, (In English).
Shuji Kondo et al: "Enhangement of Transdermal Delivery By . . . ", In J. Pharmacobio–Dy., 10, 743–749 (1987).

* cited by examiner

Primary Examiner—Thurman K. Page
Assistant Examiner—Isis Ghali
(74) Attorney, Agent, or Firm—Michael J. Striker

(57) ABSTRACT

The transdermal system includes a sex hormone-containing adhesive matrix, which contains inclusions of a sex hormone in a hydrophilic non-crosslinked polymer in dissolved or dispersed form. The inclusions have a concentration of 20 to 90 percent by weight of the sex hormone, which is more than 50 percent by weight amorphous. The hydrophilic non-crosslinked polymer can be polyvinylpyrrolidone, methylcellulose, ethylcellulose or hydroxyethylcellulose. The adhesive matrix can be a polyisobutylene, ethylene-vinyl-acetate copolymer or a polystyrene-butadiene block copolymer.

15 Claims, No Drawings

LAMINATES CONTAINING AN ACTIVE SUBSTANCE TRANSDERMAL SYSTEM

BACKGROUND OF THE INVENTION

1. Field of the Invention

The invention relates to laminates containing substance for transdermal systems.

2. Description of the Related Art

The treatment of chronic diseases by administration of highly active drugs is a recognized method of treatment well accepted by patients. In particular, the treatment of hormone deficiencies with estrogens or testosterone, besides the administration of strong analgesics, is a rapidly growing segment of the pharmaceutical market.

A problem common to all transdermal forms of administration is the need to overcome the diffusion barrier of the skin and to maintain therapeutically effective blood levels.

Transdermal systems such as active substance-containing adhesives, bandages and the like are often used as are creams and ointments. These systems, sold in different technical embodiments such as matrix systems or reservoir systems, are well known to those skilled in the art of transdermal administration of active substances. In general, reservoir systems contain solutions of active pharmaceutical substances in a liquid, highly volatile solvent such as ethanol, capable of increasing permeation through the intact skin. By contrast, the drug-in-adhesive or matrix systems do not employ these volatile solvents. Instead, they use absorption enhancers that are soluble in the matrix and do not volatilize during the preparation process.

Absorption accelerators for matrix systems are typically lipophilic, low-volatile liquids, such as fatty esters, medium- or long-chain alcohols, emulsifiers, terpenes and the like. Their action is based on the following essential mechanisms:

a) they disturb the diffusion-hindering structures of the lipid double-layers of the stratum corneum, or b) they increase the concentrations/saturation concentrations of the drugs in the stratum corneum.

As a result, both mechanisms increase the flux of the active substance through the skin. Particularly when the make-up of the skin structures is disturbed or destroyed, to improve permeation, the skin reacts with undesirable side effects such as reddening, itching, inflammation and the like. In severe cases, allergic reactions can occur. Only very few commercially available transdermal systems contain no absorption accelerators. The basis for diffusion through membranes—such as the skin—are Fick's diffusion laws. According to these laws, permeation through membranes is determined by the concentration gradient of the diffusing substance along the cross-section of the membrane. The gradient is created by the difference in concentration of the active substance between the donor compartment (transdermal system) and the skin. For simplicity, the skin in this case is assumed to be an ideal homogeneous membrane. Hence, skin permeation can be modified by, among other things, varying the active substance concentrations in transdermal systems. The increase in skin permeation, needed in a great majority of cases, is limited by a) the saturation solubility of the drug involved in the adhesive-active substance solution used to prepare the transdermal system or b) the saturation solubility in the adhesive matrix.

In the following, the two cases are described separately.

A) In the predominant number of cases, the drugs are either dissolved in the solutions of the adhesives in organic solvents such as ethyl acetate, acetone, hexane or heptane directly or with the addition of compatible solvents. The amount of solvent that can be added to the adhesive solutions to be able to predissolve the active substances therein is limited by the compatibility with the adhesive solutions involved or by the resulting dilution of the adhesive solids content. In practice, the coating methods known to those skilled in the art make it possible to process only adhesive solutions with a defined minimum viscosity and solids content. Nonpolar solvents, in particular, which are used for processing nonpolar polymers such as polyisobutylene, have only slight dissolution power for active substances such as sex hormones, antihypertensive agents, analgesics etc. As a rule, the dissolution power is not sufficient to produce adhesive matrices with optimum active substance loading after the solvent has evaporated. Even in acrylate adhesives, which are mainly processed from ethyl acetate-containing solvent mixtures, the dissolution power is not sufficient to dissolve, for example, derivatives of sex hormones, such as ethinylestradiol, levonorgestrel and the like in quantities that would be necessary to produce a sufficient concentration gradient between the transdermal system and the skin.

B) In practice, if sufficient concentrations of the active substance can be achieved, supersaturated and thus metastable conditions of the embedded active substances very often arise in the dried matrix. The drugs in such metastable matrices tend to recrystallize on storage, such crystallization resulting in a decrease in active substance concentration and thus in a decrease of the concentration gradient. Moreover, the adhesive properties of the recrystallized matrix can change to become very unfavorable, in some cases rendering the matrix unusable. Even polymers with a very high dissolution power cannot dissolve, for example, more than 2.5–3% of sex hormones in a stable manner. Permeation experiments with highly supersa-turated adhesive matrices have shown that the skin allows higher quantities of hormones to permeate than stable saturated or unsaturated transdermal systems permit. Thus, the limiting step is not the permeation capacity of the skin but the active substance loading of the stable matrices.

To prevent the use of—potentially—harmful absorption enhancers in transdermal systems and to realize high flow rates that will result in reliable blood levels, a technology is needed which will permit the production of transdermal systems with high active substance loading and good storage stability.

It is known from the prior art to embed an active substance in a polymer for the purpose of modifying and controlling its release properties. The prior-art describes the use of polymers to stabilize super-saturated conditions in transdermal systems [TDS] (J. Pharmacobio-Dyn. 10, 743, 1987). German Patent DE 4 334 553 A1 discloses increasing the flow rate by means of a supersaturated condition. On prolonged storage or prolonged duration of application, such supersaturations in energy-rich structures, however, can cause instabilities thus putting a time limit on the system's usefulness.

European Patent EP 0 516 141 A1 describes a bioadhesive pharmaceutical preparation in which active substance-bearing microunits, including embedded polymer particles, are compressed together with adhesive polymers and various other auxiliary agents and comminuted to form granules. Although this use comprises the idea of employing granular polymer inclusions independently of the adhesive component thus achieving greater flexibility in controlling active substance release after application, the technology proposed here is not suitable for the production of stable laminates for TDS in terms of either their objective or the method of preparation.

EP 0 481 443 A1 discloses the use of microporous particles or microspheres of chemically crosslinked polymers as carriers for the active substance and/or the absorption enhancer. The limited loadability of the microspheres with active substance, imparted by the preparation technology, and the use of crosslinked polymers, however, generate only a limited active substance diffusion pressure through the skin so that, here, too, it is necessary to use additional absorption enhancers. The systems described in DE 4 405 898 A1, EP 0 674 900 A1 and DE 19701949 A1 have the same drawback. These systems use the active substance together with a nonadhesive polymer which acts as crystallization retarder and to which adhesive properties are later imparted by chemical or physical mechanisms.

U.S. Pat. No. 5,656,286 describes the use of soluble polyvinyl chloride [PVC] in admixture with polyvinylpyrrolidone for the purpose of preventing the crystallization of the active substances, but the active substance release rate is not improved.

U.S. Pat. No. 5,702,721 describes a matrix which comprises an impermeable backing layer, a matrix with an active substance that can be activated and a layer which regulates the access of liquid. The matrix consists of a material which is permeable to water vapor but in itself is not water-soluble and contains no active substance. Included in this matrix are "islands" of water-soluble or water-swellable material loaded with active substance. The loading of unloaded islands can be achieved by solid-liquid absorption or by special drying methods. The complicated structure and process of producing this multilayer system represents a drawback. A special mechanism for regulating the access of skin moisture is needed, because otherwise the active substance precipitates or the release of active substance is insufficient.

SUMMARY OF THE INVENTION

The object of the invention therefore is to provide active substance-containing laminates for transdermal systems which are capable of overcoming the afore-described drawbacks of the prior art, namely which, in particular, exhibit high active substance loading and good storage stability.

This objective is reached by use of an active substance-containing laminate comprising an active substance inclusion consisting of a hydrophilic non-crosslinked polymer and an active substance included in said polymer, and a polymeric adhesive matrix into which said included active substance is incorporated.

The preparation of the active substance inclusion is carried out by a process which in itself is known, for example by drawing out a film of active substance and hydrophilic polymer and then grinding, or by spray-drying or spray-granulation technology. According to the invention, the active substance is preferably included into the polymer matrix at a high loading and in thermodynamically highly active form as a solid solution by spray-drying or spray-granulation technology, for example by the process described in WO 98/26762, rather than by other common technologies, and produced as a microfine powder with or without carrier.

According to the invention, the form of the active substance contained in the inclusion is preferably amorphous to an extent of more than 50 wt. %. It is particularly preferred if the form of the active substance contained in the inclusion is amorphous to an extent of more than 95 wt. %. The measurement and the quantification of crystallinity of the active substance is performed in the known manner by x-ray powder diffractometry (XRPD) using the corresponding crystalline modification of the active substance as a control.

It is also preferred according to the invention that the active substance concentration in the inclusion be from 5 to 90 wt. % and particularly from 20 to 40 wt. %.

The active substance-containing laminate for transdermal systems according to the invention is also characterized in that the active substance inclusion is contained in the adhesive matrix in dissolved form. Also according to the invention, however, the active substance inclusion is uniformly incorporated into the adhesive matrix in the form of finely dispersed solid particles.

The active substances contained in the laminate according to the invention can be selected almost at will. Preferred are hormones, local anesthetics, analgesics, antibiotics, neuroleptics, cytostatics, diuretics, gastrointestinal agents, cardiovascular agents, immunomodulators, immunosuppressants and vitamins or mixtures thereof. Particularly preferred are hormones, particularly sex hormones, such as estrogens, for example estradiol, estradiol esters such as estradiol valerate, estradiol 3-benzoate, the valerate, cypionate, undecanoate and enanthate of 17-estradiol, estradiol sulfamate, ethinylestradiol sulfamate and 3-estrone sulfamates, for example estrone N,N-dimethylsulfamate, estrone N,N-diethylsulfamate, 3-ethinylestradiol N,N-dimethylsulfamate, 3-ethinylestradiol N,N-diethylsulfamate, 3-ethinylestradiol N,N-tetramethylenesulfamate, estrone sulfamate, 3-estradiol sulfamate, 3-estradiol N,N-dimethylsulfamate, 3-estradiol N,N-diethylsulfamate, 3-ethinylestradiol sulfamate (DE 44 29 398 A1 and DE 44 29 397 A1), gestagens such as dienogest, desogestrel and drospirenone, antigestagens, for example those described in DE 43 32 284, DE 43 32 283 and 198 09 845.6, for example {4-[17β-methoxy-17α-(methoxymethyl)-3-oxoestra-4,9-dien-11β-yl]benzaldehyde-(1E)-oxime}, {4-[17β-hydroxy-17α-(methoxymethyl)-3-oxoestra-4,9-dien-11β-yl]benzaldehyde-(1E)oxime}, {4-[17β-methoxy-17α-(methoxymethyl)-3-oxoestra-4,9-dien-11β-yl]benzaldehyde-(1E)-[O-(ethoxy)carbonyl]oxime}, {4-[17β-methoxy-17α-(methoxymethyl)-3-oxoestra-4,9-dien-11β-yl]benzaldehyde-(1E)-[O-acetyl]oxime}, {4-[17β-methoxy-17α-(methoxymethyl)-3-oxoestra-4,9-dien-11β-yl]benzaldehyde-1E)-[O-ethylamino)-carbonyl]oxime}, {4-[17β-methoxy-17α-(methoxymethyl)-3-oxoestra-4,9-dien-11β-yl]benzaldehyde-(1E)-[O-(ethylthio)carbonyl]oxime}, and androgens, such as testosterone, testosterone undecanoate and dehydroepiandrosterone (DHEA).

According to the invention, the hydrophilic polymer is selected from the group consisting of non-crosslinked hydrophilic polymers, the polymer for inclusion, in particular, being selected from the group consisting of polyvinylpyrrolidone, methylcelluloses, ethylcelluloses, hydroxypropylcelluloses or mixtures thereof.

It is also preferred according to the invention that the adhesive matrix be selected from the group consisting of polyisobutylene, ethylene-vinyl copolymers (poly-EVA[1], polystyrene-butadiene block copolymers or mixtures thereof, or from the group consisting of pressure-sensitive adhesives based on acrylate or silicone.

[1] EVA=ethylene–vinyl acetate–Translator

Surprisingly, we have now found that the use of highly concentrated active substance inclusions in nonadhesive polymers, such as polyvinylpyrrolidone, ethylcellulose, hydroxypropylcellulose and the like can solve all above-described problems of the prior art at the same.

By the technology of the invention, specially conditioned, highly concentrated active substance inclusions into polymers are used in a manner such that the high concentrations are reached primarily for active substances that do not dissolve readily in the adhesive patch matrix without the occurrence of undesirable recrystallizations such as in the case of supersaturated solutions. The use of such highly loaded, thermodynamically highly active substance-polymer combinations in a simple-to-prepare single-layer TDS not requiring an absorption enhancer with the purpose of maximally increasing the concentration gradient between the TDS and the skin has thus far not been described in the literature.

Whereas EP 0516141 A1 describes a solid biodahesive mixture with active substance release retarded in accordance with the application involved, the technology according to the invention aims at the highest possible and stable active substance concentrations in the adhesive laminate matrix before and during the application.

This can be achieved in two ways:

A) Whereas the gestagenic hormone gestodene dissolves in ethyl acetate only to the extent of 3%, by use of, for example, a 20% solid inclusion of gestodene in polyvinylpyrrolidone the solubility in ethyl acetate/polymer mixtures can be increased to 10–15% without increasing the recrystallization. In this manner, by use of solid polymer inclusions, optimum active substance loadings can be attained in different polymers. The active substance concentrations in the polymer inclusions can be stabilized at a very high level so that only minimum amounts of additional solvent are needed. In cases where the solubility of the drug in the adhesive is the primary factor limiting skin permeation, the method of preparation described under B) must be chosen.

B) The permeation of the active substance can be additionally increased by incorporating the highly concentrated active substance-polymer inclusions into adhesives in which they do not dissolve. Such matrices can be prepared, for example, by mixing micronized active substance-polymer inclusions in polyvinylpyrrolidone with a polyisobutylene/resin mixture in n-heptane. Here the adhesive acts only as the agent that fixes the polymer inclusion to the skin. The active substance concentrations in the polymer inclusions can definitely exceed 50%.

The use of solid active substance inclusions in appropriate nonadhesive polymers is a prerequisite for achieving high active substance concentrations in the adhesive matrix while preventing recrystallization phenomena. Suitable nonadhesive polymers are polyvinylpyrrolidones, methylcellulose, ethylcellulose, hydroxypropylcellulose and others. This listing is not limitative. These solid active substance inclusions can be used in the adhesive matrix advantageously in dissolved or dispersed, solid form. The active substance loading of the solid polymer inclusions depends on the above-indicated uses and on the permeation requirements. Depending on the type of active substance-polymer combination used, the active substance loaded is completely or mostly amorphous to an extent of more than 50%.

When such solid active substance inclusions are introduced into adhesive matrix solutions in dissolved form, the high solubility of the inclusion polymer in the matrix solvent used, for example ethyl acetate, ethanol etc, is important. Rapid dissolution of the amorphous active substance is attained to a level far above its saturation solubility in the pure solvent. For example, at room temperature ethyl acetate dissolves only about 3 wt. % of a gestagenic steroid. By use of a corresponding solid active substance solution, the solubility of the steroid in the solution of ethyl acetate and nonadhesive polymer was increased to nearly 15 wt. % and kept stable. It should be kept in mind in this respect that, based on the volatile solvent ethyl acetate which is to be driven off from the adhesive matrix that is to be dried, the solubility was increased to more than 30 wt. %. The polymer here inhibits the crystallization in the highly supersaturated adhesive solution and later, after drying, in the adhesive active substance matrix.

The magnitude of the permissible active substance loading depends on this inhibitory activity which, in turn is affected by the choice of the inclusion polymer, the active substance itself and the polar solvent used. The inhibition effect decreases with increasing amount of active substance. For example, in the case of a gestagenic steroid, loadings of more than 20% in a polyvinylpyrrolidone resulted in recrystallization phenomena in the ethyl acetate solution. When an estrogenic steroid was used, substantially higher loadings were possible in the same system. Another important aspect is the degree of amorphousness of the active substance in the solid polymer inclusion. This degree is preferably 100% or close to 100%, because an active substance containing recrystallized material does not dissolve completely in the supersaturated solution and can promote recrystallization. The particle size distribution has no relevance for this application.

The situation is different when solid active substance inclusions are used in the form of solid particles finely dispersed and uniformly distributed in the pressure-sensitive adhesive polymer. These solid active substance inclusions are nearly insoluble in the adhesive matrix solution. Their active substance loading is adjusted depending on permeation requirements and is only limited by the requirement that the active substance be present in completely or at least mostly amorphous form and that this amorphous part remain stable, i.e. not recrystallize, during storage, during processing and while dispersed in the adhesive polymer. Depending on the type of active substance/polymer combination used, above a certain loading the capacity of the polymer for a stable amorphous status of the active substance is exhausted. For example, with a hydroxypropylcellulose and collidone[2], it is possible to prepare stable, predominantly amorphous inclusions of estrogenic and gestagenic steroids with up to 80% of active substance. Because the inhibiting function concerning the recrystallization of the active substance dissolved in the adhesive polymer is not required for this use, the amorphization capacity of the polymer can be fully exhausted. In this manner, when necessary, a very high concentration of the amorphous and finely dispersed active substance can be attained in the adhesive patch matrix without running the risk of recrystallization.

[2] Collidone=povidone=polyvinylpyrrolidone–Translator

Moreover, this process offers the possibility of protectively embedding chemically sensitive, unstable active substances up to the time of their permeation, or of embedding several active substances with different permeation requirements isolated from each other, so to speak in tailor-made fashion, and thus utilize them in a single patch.

The average particle size of the solid polymer inclusions is less than 10 μm and preferably less than 5 μm, namely in the range of that of micronized active substances. These solid polymer inclusions are prepared by processes of conventional pharmaceutical technology.

According to the invention, the solid active substance-polymer inclusions are used to increase the active substance concentration in coating solutions.

Solutions of pressure-sensitive acrylate-based adhesives, obtainable from different manufacturers (examples are Duro-Tak adhesives by National Starch & Chemical Corporation, or various Gelva products by Monsanto, or the silicone adhesives such as Bio PSA by Dow Corning and the like), are uniformly mixed with highly concentrated active substance solutions in medium-polar solvents, such as ethyl acetate or alcohols.

These highly concentrated solutions are obtained by dissolving solid polymer-active substance inclusions in nonadhesive polymers the preparation of which has been described hereinabove.

Optionally, the resulting solutions are adjusted to the required viscosity and/or solids content by use of additional additives. The solutions can be applied to siliconized foils, paper or the like by conventional coating methods known to those skilled in the art, for example by use of a doctor blade, reverse roll coating, spraying and the like. The coated substrate is freed of the volatile solvent in a drying facility, such as a drying tunnel or drying oven, and the resulting self-adhesive matrix is laminated with a backing foil, fabric or non-woven fabric or the like. The laminate is rolled up and either cut into narrower rolls or directly stamped out or die-cut in conventional stamping machines to form defined individual pieces, namely the transdermal system. According to the invention, no layer facing the skin is needed to control the entry of the cutaneous liquid.

For protected storage, the transdermal systems can be packed into pouches. Each of the above-indicated polymers (acrylates, silicones and the like) have different dissolution capacities for active substances, depending on their composition. By use of the preparation technology of the invention, the saturation concentrations of the active substances involved can be attained in different pressure-sensitive adhesives. In this manner, active substance fluxes can be optimized for each adhesive.

According to the invention, the solid active substance-polymer inclusions are also used in combination with inert pressure-sensitive adhesives.

The active substance-containing polymer inclusions have been described in the foregoing. The solid active substance inclusions are used as powders of varying particle size and even as micronized powders. The powdered inclusions are suspended in nonpolar solvents such as hexane, heptane or the like and uniformly mixed with nonpolar solutions of pressure-sensitive adhesives, such as polyisobutylene, poly-EVA, polystyrene-butadiene block copolymers or the like. The solutions can contain other common additives, such as antioxidants, adhesive resins, plasticizers, dissolution enhancers or the like, required for preparing stable, well-adhering, skin-compatible transdermal systems. The solid active substance-polymer inclusions should not dissolve substantially in these solvents. The powders are mixed with the adhesive preparations until homogeneous. The coating, drying and lamination are carried out as described hereinabove.

The resulting matrix consists of a pressure-sensitive adhesive polymer which acts as the element whereby the transdermal system i.e., the active substance reservoir and the uniformly distributed active substance-polymer inclusion particles, is fixed to the skin. Ideally, the adhesive polymer should not interact with the polymer inclusion.

If these prerequisites are met, the active substance permeation through membranes made of the transdermal system of the invention is determined essentially by the type of polymer of the active substance inclusion and by the active substance concentration in the inclusion. In this manner, active substance concentrations in transdermal systems (TDS) can be achieved which exceed by far those directly attainable in the adhesives. Because the active substances are not dissolved in the adhesives, and during storage the adhesives can absorb the active substance only to the extent of their maximum solubility, there is no danger of recrystallization of the conventional systems.

The active substance permeation can be controlled by various measures:
- particle size of the active substance-polymer inclusion
- active substance concentration in the active substance-polymer inclusion
- number of particles of the active substance-polymer inclusion per volume element of the adhesive
- release surface area of the transdermal system
- solubility of the active substance in the inclusion polymer
- interaction of the active substance-polymer inclusion with the adsorbate water from the skin
- crystallinity of the active substance in the active substance-polymer inclusion.

At a high active substance flux without absorption accelerator, transdermal systems according to the invention are characterized in that a high active substance concentration, in some cases higher than 80%, can be reached in the particles of the active substance-polymer inclusion. Thus, the polymers used for the inclusion can be selected on the basis of their best ability to stabilize high amounts of active substance independently of their adhesive power, cold flow or the like. Hence, undesirable recrystallization can be prevented even at concentrations above 50 wt. %.

The active substance-polymer inclusion disperses in the polymeric adhesive matrix without dissolving therein. This means that the properties of the highly concentrated polymer inclusion are essentially retained in finished matrix systems. In this manner, a high active substance gradient is created between the polymer inclusion and the skin. This gradient is much greater than when the active substance is uniformly dispersed in a mixture of inclusion polymer and adhesive matrix. For example, when 10 mg of an 80% active substance inclusion is dispersed in 90 mg of adhesive matrix, the active substance concentration within the active substance inclusion is 80% as before, whereas when the active substance is completely dissolved in the overall matrix, the concentration is only 8%.

The following example will explain the invention.

EXAMPLES

Example 1

Solid active substance-polymer inclusion for increasing the concentration of the active substance dissolved in the adhesive matrix:
20% of gestodene
80% of collidone
Particle size distribution:
100%<103 µm
50%<24 µm
10%<4.3 µm
Amorphousness of the active substance: 100% (XRPD)

Example 2

Solid active substance-polymer inclusion for preparing a uniform, finely dispersed suspension in the adhesive matrix:
30% of gestodene
70% of collidone
Particle size distribution:
100%<21 µm
50%<3.7 µm
10%<1.1 µm
Amorphousness of the active substance: 100% (XRPD)

Example 3

Transdermal system with a uniform, finely dispersed suspension in the adhesive matrix:

10 g of the polymer inclusion described in Example 2 was uniformly dispersed in 169.7 g of a commercial polyisobutylene adhesive. The dispersion was applied to an 80-$\mu$m-thick siliconized polyester foil by conventional coating methods such as by the use of a doctor blade, and dried. Drying produced a self-adhesive matrix with a weight per unit area of 100 g/m$^2$ and with 5.1% of gestodene in the matrix. The self-adhesive matrix was covered with, for example, a 19-$\mu$m-thick backing foil, and the laminate was processed to transdermal systems with a surface area of, for example, 10 cm$^2$. A transdermal system made in this manner shows an in-vitro skin permeation of 40.3 $\mu$g of gestodene/cm$^2$/24 h, determined in diffusion cells on intact skin of nude mice.

Example 4

Solid active substance-polymer inclusion made by the following method:

100 g of gestodene and 150 g of collidone (VA64) were dissolved in 2360 g of ethanol, and the solution was spray-dried at 64–65° C. at a rate of 32 mL of solution per m$^3$ of drying gas. A microfine powder with the following parameters was obtained:

Particle size distribution:

100%<20 $\mu$m
90%<6.4 $\mu$m
50%<2.8 $\mu$m
10%<1.0 $\mu$m
XRPD: 100% amorphous
Ethanol: 0.84%

What is claimed is:

1. A transdermal system comprising a substrate and a sex hormone-containing adhesive matrix, wherein said sex hormone-containing adhesive matrix contains solid inclusions in dissolved form or dispersed form, said solid inclusions consist of a hydrophilic non-crosslinked polymer and a sex hormone, said solid inclusions have a concentration of said sex hormone of 20 to 90 percent by weight and said sex hormone is more than 95 percent by weight amorphous.

2. The transdermal system according to claim 1, wherein said solid inclusions are present in the adhesive matrix in said dissolved form.

3. The transdermal system according to claim 1, wherein said solid inclusions are present in the adhesive matrix in said dispersed form.

4. The transdermal system according to claim 1, wherein said hydrophilic non-crosslinked polymer is polyvinylpyrrolidone, methylcellulose, ethylcellulose, hydroxyethylcellulose, or mixtures thereof.

5. The transdermal system according to claim 1, wherein said adhesive matrix comprises at least one material selected from the group consisting of polyisobutylenes, ethylene-vinyl-acetate copolymers and polystyrene-butadiene block copolymers.

6. The transdermal system according to 1, wherein said sex hormone in said solid inclusions is 100 percent by weight amorphous, as determined by X-ray powder diffraction measurements.

7. The transdermal system according to one of claims 1 and 6, wherein said solid inclusions contain more than 50 percent by weight of said sex hormone, but not more than 90 percent by weight of said sex hormone.

8. A transdermal system comprising a substrate and a sex hormone-containing adhesive matrix, wherein said sex hormone-containing adhesive matrix contains dispersed solid inclusions and said solid inclusions consist of a hydrophilic non-crosslinked polymer and a sex hormone, said solid inclusions have a concentration of said sex hormone of 20 to 90 percent by weight and said sex hormone is more than 95 percent by weight amorphous.

9. The transdermal system according to claim 8, wherein said hydrophilic non-crosslinked polymer is polyvinylpyrrolidone, methylcellulose, ethylcellulose, hydroxyethylcellulose, or mixtures thereof.

10. The transdermal system according to claim 8, wherein said adhesive matrix comprises at least one polymeric adhesive material selected from the group consisting of polyisobutylenes, ethylene-vinyl-acetate copolymers and polystyrene-butadiene block copolymers.

11. A transdermal system comprising a substrate and a sex hormone-containing adhesive matrix, wherein said sex hormone-containing adhesive matrix is formed by dissolving solid inclusions in a polymeric adhesive, said solid inclusions consist of a hydrophilic non-crosslinked polymer and a sex hormone, said solid inclusions have a concentration of said sex hormone of 20 to 90 percent by weight and said sex hormone Is more than 95 percent by weight amorphous.

12. The transdermal system according to claim 11, wherein said hydrophilic non-crosslinked polymer is polyvinylpyrrolidone, methylcellulose, ethylcellulose, hydroxyethylcellulose, or mixtures thereof.

13. The transdermal system according to claim 11, wherein said polymeric adhesive is selected from the group consisting of polyisobutylenes, ethylene-vinyl-acetate copolymers and polystyrene-butadiene block copolymers.

14. The transdermal system according to one of claims 1, 8 and 11, containing no absorption accelerators or enhancers for increasing a flux of said sex hormone through skin.

15. The transdermal system according to claim 8 or 11, wherein said sex hormone in said solid inclusions is 100 percent by weight amorphous, as determined by X-ray powder diffraction measurements.

* * * * *